US009572836B2

(12) United States Patent
June et al.

(10) Patent No.: US 9,572,836 B2
(45) Date of Patent: Feb. 21, 2017

(54) METHODS FOR ASSESSING THE SUITABILITY OF TRANSDUCED T CELLS FOR ADMINISTRATION

(71) Applicant: The Trustees of the University of Pennsylvania, Philadelphia, PA (US)

(72) Inventors: Carl H. June, Merion Station, PA (US); Bruce L. Levine, Cherry Hill, NJ (US); Michael D. Kalos, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/412,844

(22) PCT Filed: Jul. 12, 2013

(86) PCT No.: PCT/US2013/050287
§ 371 (c)(1),
(2) Date: Jan. 5, 2015

(87) PCT Pub. No.: WO2014/011996
PCT Pub. Date: Jan. 16, 2014

(65) Prior Publication Data
US 2015/0190428 A1 Jul. 9, 2015

Related U.S. Application Data

(60) Provisional application No. 61/671,495, filed on Jul. 13, 2012.

(51) Int. Cl.
*C12Q 1/04* (2006.01)
*A61K 35/17* (2015.01)
*C12Q 1/70* (2006.01)
*G01N 33/569* (2006.01)
*G01N 33/92* (2006.01)
*C07K 16/28* (2006.01)

(52) U.S. Cl.
CPC ........... *A61K 35/17* (2013.01); *C07K 16/2803* (2013.01); *C12Q 1/04* (2013.01); *C12Q 1/701* (2013.01); *G01N 33/569* (2013.01); *G01N 33/56933* (2013.01); *G01N 33/56983* (2013.01); *G01N 33/92* (2013.01); *C07K 2317/622* (2013.01); *C12Q 2600/158* (2013.01); *G01N 2333/195* (2013.01); *G01N 2333/37* (2013.01); *G01N 2400/50* (2013.01)

(58) Field of Classification Search
None
See application file for complete search history.

(56) References Cited

U.S. PATENT DOCUMENTS

| | | |
|---|---|---|
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 2003/0215427 A1 | 11/2003 | Jensen |
| 2004/0101519 A1 | 5/2004 | June et al. |
| 2006/0034810 A1 | 2/2006 | Riley et al. |
| 2006/0121005 A1 | 6/2006 | Berenson et al. |
| 2006/0246548 A1* | 11/2006 | Jensen .................. C07H 21/04 435/69.1 |
| 2009/0285861 A1 | 11/2009 | Wu et al. |

FOREIGN PATENT DOCUMENTS

| | | |
|---|---|---|
| WO | WO 01/29058 | 4/2001 |
| WO | WO 01/96584 | 12/2001 |
| WO | WO 2012/079000 | 6/2012 |

OTHER PUBLICATIONS

Berg et al., "Selective expansion of a peripheral blood CD8+ memory T cell subset expressing both granzyme B and L-selectin during primary viral infection in renal allograft recipients." Transplant Proc. 30(8):3975-3977, 1998.
Bierer et al., "Cyclosporin A and FK506: molecular mechanisms of immunosuppression and probes for transplantation biology." Curr. Opin. Immun. 5:763-773, 1993.
Bird et al., "Single-chain antigen-binding proteins." 1988, Science 242:423-426.
Brentjens et al., "Treatment of chronic lymphocytic leukemia with genetically targeted autologous T cells: case report of an unforeseen adverse event in a phase I clinical trial." 2010, Molecular Therapy, 18:4, 666-668.
Dropulic et al., "Gene-based immunotherapy for human immunodeficiency virus infection and acquired immunodeficiency syndrome." 2006, Human Gene Therapy, 17: 577-88 (Abstract).
Dull et al., "A third-generation lentivirus vector with a conditional packaging system." 1998, J Virol, 72: 8463-71.
Garland et al., "The use of Teflon cell culture bags to expand functionally active CD8+ cytotoxic T lymphocytes." J. Immunol Meth. 227(1-2):53-63, 1999.
Haanen et al., "Selective expansion of cross-reactive CD8(+) memory T cells by viral variants." J. Exp. Med. 190(9):13191328, 1999.
Henderson et al., "Comparison of the effects of FK-506, cyclosporin A and rapamycin on IL-2 production." Immun. 73:316-321, 1991.
Houston et al., "Protein engineering of antibody binding sites: recovery of specific activity in an anti-digoxin single-chain Fv analogue produced in *Escherichia coli*." 1988, Proc. Natl. Acad. Sci. USA 85:5879-5883.
Jena, et al., "Redirecting T-cell specificity by introducing a tumor-specific chimeric antigen receptor." Blood, 2010, 116:1035-1044.
Liu et al., "Calcineurin is a common target of cyclophilin-cyclosporin A and FKBP-FK506 complexes." Cell 66:807-815, 1991.
Macallan et al., "Measurement and modeling of human T cell kinetics." 2003, Eur J Immunol, 33: 2316-26 (abstract).

(Continued)

Primary Examiner — Brian J Gangle
(74) Attorney, Agent, or Firm — Saul Ewing LLP; Kathryn Doyle

(57) ABSTRACT

The invention relates to of analyzing vector supernatants useful for transducing T cells destined for administration to a human subject. The invention also related to methods of analyzing transduced T cells destined for administration to a human subject.

14 Claims, 6 Drawing Sheets

(56) References Cited

OTHER PUBLICATIONS

Milone et al., "Chimeric receptors containing CD137 signal transduction domains mediate enhanced survival of T cells and increased antileukemic efficacy in vivo." 2009, Mol Ther, 17: 1453-64.
Morgan et al., "Case report of a Serious Adverse Event Following the Administration of T Cells Transduced with a Chimeric Antigen Receptor Recognizing ERBB2." 2010, Molecular Therapy, 18(4):843-851.
Mumtaz et al., "Design of liposomes for circumventing the reticuloendothelial cells." 1991 Glycobiology 5: 505-10.
Naldini et al., "In vivo gene delivery and stable transduction of nondividing cells by a lentiviral vector." 1996, Science, 272: 263-7.
Porter et al, "A phase 1 trial of donor lymphocyte infusions expanded and activated ex vivo via CD3/CD28 costimulation." 2006, Blood, 107:1325-31.
Roederer, "T-cell dynamics of immunodeficiency." 1995, Nat Med, 1: 621-7.
Rosenberg et al., "Use of tumor-infiltrating lymphocytes and interleukin-2 in the immunotherapy of patients with metastatic melanoma. A preliminary report." New Eng. J. of Med. 319:1676, 1988.
Till et al., "Adoptive immunotherapy for indolent non-Hodgkin lymphoma and mantle cell lymphoma using genetically modified autologous CD20-specific T cells." 2008, Blood, 112:2261-2271.
Uckun, et al. "Detailed studies on expression and function of CD19 surface determinant by using B43 monoclonal antibody and the clinical potential of anti-CD19 immunotoxins." Blood, 1988, 71:13-29.
Ui-Tei et al., "Sensitive assay of RNA interference in *Drosophila* and Chinese hamster cultured cells using firefly luciferase gene as target." 2000 FEBS Letters 479: 79-82.
Zufferey et al., "Multiply attenuated lentiviral vector achieves efficient gene delivery in vivo." 1997, Nature Biotechnol 15:871-875.
International Search Report issued Dec. 2, 2013—PCT/US2013/050287.
Eurasian Region Patent Application No. 201590216/28—Office Action issued May 4, 2016.
Porter et al., "Chimeric antigen receptor-modified T cells in chronic lymphoid leukemia." 2011 New Engl J Med 365(8):725-733.
Scholler et al., "Decade-long safety and function of retroviral-modified chimeric antigen receptor T cells." 2012, Sci Transl Med 4(132):132ra53.
European Patent Application No. 13817548—European Search Report dated Mar. 11, 2016.

\* cited by examiner

| Test | Method | Criteria | Sensitivity | Specificity |
|---|---|---|---|---|
| Cell Viability on Sentinel Tube | Trypan Blue Exclusion | ≥70% | N/A | N/A |
| % CD3 positive T cells | Flow Cytometry | ≥80% | 1 in 20,000 cells | CD3+ cells |
| Residual beads number | Visual | ≤100 beads/3e6 cells | 1 bead/3e6 cells | Not applicable |
| Endotoxin | Gel Clot | ≤ 3.5 EU/mL | 0.125EU/mL | Gram-negative bacterial endotoxin |
| Mycoplasma | MycoAlert Assay | Negative | <50 cfu/mL | mycoplasma |
| RCL (HIV$_{gag}$) | PCR | Negative | ≥30 copies/μg genomic DNA | HIV gag 1299-1377(region absent in lentiviral vector) |
| Transduction efficiency (scFv expression) | Flow Cytometry | ≥20% positive | 1 in 20,000 cells | Murine single chain variable fragment |
| HIV-1 P24 Antigen ELISA | ELISA | < 10 pg/mL | 0-4000 pg/mL | HIV-1 p24 core antigen in human serum, plasma, cell culture supernatant |
| Transduction efficiency (copy number) | QT-PCR | ≥0.2 average copies per cell | 10 copies/μg genomic DNA | CART-19 vector specific region of the CAR intracellular signaling domain |
| VSV-G DNA | QT-PCR | Negative | 25 copies/μg genomic DNA | G protein of VSV |
| BSA | ELISA | ≤1 μg/ml | 250 pg/mL | BSA |
| Bacterial culture | Culture | No growth | TBD | -Alcaligenes faecalis<br>-Candida albicans<br>-Escherichia coli<br>-Haemophilus influenzae<br>-Neisseria meningitidis<br>-Pseudomonas aeruginosa<br>-Staphylococcus aureus<br>-Streptococcus pneumoniae<br>-S. pyogenes group A |
| Fungal culture | Culture | No growth | TBD | To be determined |

METHODS FOR ASSESSING THE SUITABILITY OF TRANSDUCED T CELLS FOR ADMINISTRATION

CROSS-REFERENCE TO RELATED APPLICATION

This application is the U.S. national phase application filed under 35 U.S.C. §371 claiming benefit to International Patent Application No. PCT/US2013/050287 filed on Jul. 12, 2013, which is entitled to priority under 35 U.S.C. §119(e) to U.S. Provisional Application No. 61/671,495, filed Jul. 13, 2012, each of which is hereby incorporated by reference in its entirety.

STATEMENT REGARDING FEDERALLY SPONSORED RESEARCH OR DEVELOPMENT

This invention was made with government support under grant numbers K24 CA11787901, 1PN2-EY016586, 1R01CA105216, 1R01CA120409, RO1AI057838, and R01113482, awarded by the National Institutes of Health (NIH). The government has certain rights in the invention.

BACKGROUND OF THE INVENTION

The large majority of patients having B-cell malignancies, including chronic lymphocytic leukemia (CLL), will die from their disease. One approach to treating these patients is to genetically modify T cells to target antigens expressed on tumor cells through the expression of chimeric antigen receptors (CARs). CARs are antigen receptors that are designed to recognize cell surface antigens in a human leukocyte antigen-independent manner. Attempts in using genetically modified cells expressing CARs to treat these types of patients have met with very limited success. See for example, Brentjens et al., 2010, Molecular Therapy, 18:4, 666-668; Morgan et al., 2010, Molecular Therapy, published online Feb. 23, 2010, pages 1-9; and, Till et al., 2008, Blood, 112:2261-2271.

While CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity (Jena, et al., Blood, 2010, 116:1035-1044; Uckun, et al. Blood, 1988, 71:13-29). Methods of generating genetically modified T cells for administration to humans have the potential to produce unwanted contaminants that may negatively impact the persistence and function of the genetically modified T cells after administration.

Thus, there is a need in the art for analyzing transduced T cells for their suitability for administration to a human subject, through the detection of contaminants that may negatively impact the persistence and function of genetically modified cells. The present invention addresses this need.

SUMMARY OF THE INVENTION

The invention provides a method of analyzing a genetically modified T cell to detect a contaminant, wherein the genetically modified T cell comprises a nucleic acid encoding a chimeric antigen receptor (CAR), wherein the CAR comprises an antigen binding domain, a transmembrane domain, a costimulatory signaling region, and a signaling domain.

In one embodiment, the genetically modified T cell was genetically modified by transduction with a lentiviral vector.

In one embodiment, the contaminant is at least one selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus.

In one embodiment, the bacterium is at least one selected from the group consisting of *Alcaligenes faecalis, Escherichia coli, Haemophilus influenzae, Neisseria meningitidis, Pseudomonas aeruginosa, Staphylococcus aureus, Streptococcus pneumoniae*, and *Streptococcus pyogenes* group A.

In one embodiment, the signaling domain is a CD3 zeta signaling domain.

In one embodiment, the antigen binding domain is an antibody or an antigen-binding fragment thereof.

In one embodiment, the antigen-binding fragment is a Fab or a scFv.

In one embodiment, the antigen binding domain binds to a tumor antigen.

In one embodiment, the tumor antigen is associated with a hematologic malignancy.

In one embodiment, the tumor antigen is associated with a solid tumor.

In one embodiment, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

In one embodiment, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the genetically modified T cell is not administered to a human subject because of the identification and quantification of the contaminant.

In one embodiment, the genetically modified T cell is not administered to a human subject because the quantity of the contaminant is excessive as compared with a corresponding control level.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the lentiviral vectors and transgene that show the major functional elements. A vesicular stomatitis virus protein G pseudotyped clinical grade lentiviral vector (designated pELPs 19BBz) directing expression of anti-CD19 scFv derived from FMC63 murine monoclonal antibody, human CD8α hinge and transmembrane domain, and human 4-1BB and CD3zeta signaling domains was produced. Constitutive expression of the transgene was directed by inclusion of an EF-1α (elongation factor-1α promoter); LTR, long terminal repeat; RRE, rev response element. (cPPT) and the central termination sequence (CTS). Figure is not to scale. FIG. 1B depicts T cell manufacturing. Autologous cells were obtained via apheresis, and for non-CLL study subjects T cells were enriched by mononuclear cell elutriation. For CLL subjects residual leukemia cells depleted by addition of anti-CD3/CD28 coated paramagnetic beads for positive selection and activation of T cells. For non-CLL subjects, elutriated cells were washed followed by addition of anti-CD3/CD28 coated paramagnetic beads for activation of T cells. Lentiviral vector was added at the time of cell activation and was washed out on day 3 post culture initiation. Two days later, cells were expanded on a rocking platform device (WAVE Bioreactor System) for an additional 3-7 days. On the final day of culture the beads were removed by passage over a magnetic field and the CART19 T cells harvested, washed, and cryopreserved in infusible medium. Patients were given lymphodepleting chemotherapy as described, followed by CART19 infusion #1 by i.v. gravity flow drip over a period of 15-20 minutes. The infusion was given using a split dose approach over 3 days (10%, 30%, 60%) beginning 1 to 5 days after completion of chemotherapy. Endpoint assays were conducted on study week 4. At the conclusion of active monitoring, subjects were transferred to a destination protocol for long term follow up as per FDA guidance.

FIG. 3 is a table listing the types of analyses performed on the transduced T cells.

DETAILED DESCRIPTION

Figure 1A:
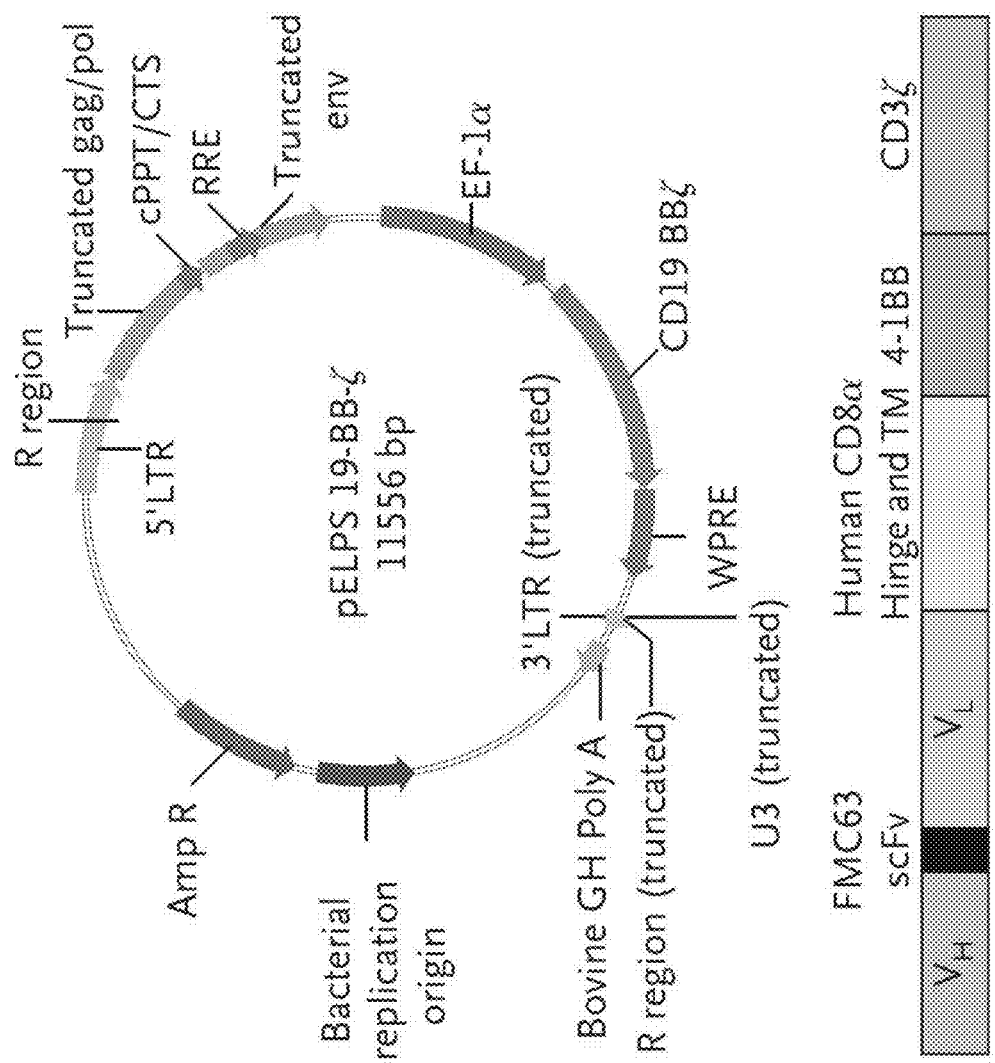
FIGS. 1A and 1B, is a series of images of the schematic representations of the gene-transfer vector and transgene, gene modified T cell manufacturing and clinical protocol design.
Figure 1B:
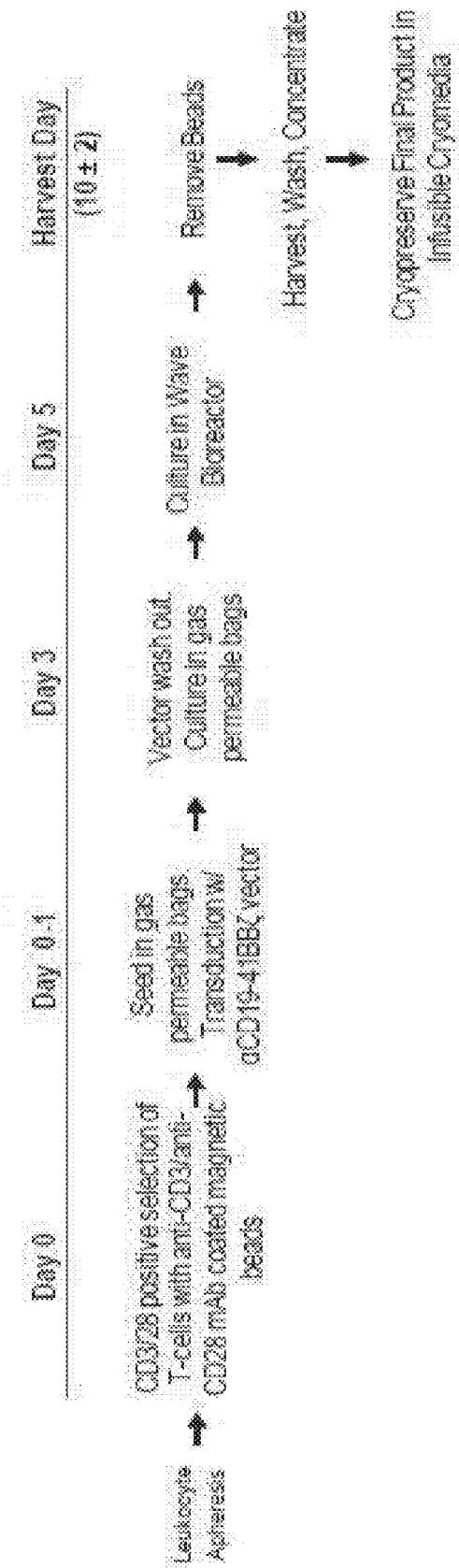

The invention relates to methods of producing vectors comprising nucleic acids encoding a chimeric antigen receptor (CAR) that are suitable for the transduction of T cells destined for the administration to a human subject. The invention also relates to methods of transducing T cells destined for the administration to a human subject with vectors comprising nucleic acids encoding a chimeric antigen receptor (CAR). In a preferred embodiment, the vector is a lentiviral vector. The present invention relates to adoptive cell transfer of T cells transduced with a lentiviral vector to express a CAR. CARs are molecules that combine antibody-based specificity for a desired target antigen (e.g., tumor antigen) with a T cell receptor-activating intracellular domain to generate a chimeric protein that exhibits a specific anti-tumor cellular immune activity.

In some embodiments, the methods of the invention relate to methods of analyzing vector supernatants useful for transducing T cells destined for administration to a human subject. In other embodiments, the methods of the invention relate to methods of analyzing transduced T cells destined for administration to a human subject. In various embodiments, the methods of analysis of the invention include methods of analyzing T cell viability, T cell character (e.g., CD3, CD4, CD8, CD25, CD27, CD45RA, CD57, CD62L, CD95, CD127, CD134, CD244. CCR7, CD40L, CTLA4, PD-1, HLA-DR, TIM3, Ki-67, perforin, and/or granzyme expression), transduction efficiency, as well as methods of detecting and quantifying contaminants associated with the manufacturing process, such as endotoxin, mycoplasma, replication competent lentivirus (RCL), p24, VSV-G nucleic acid, HIVgag, residual anti-CD3/anti-CD28 coated beads, mouse antibodies, pooled human serum, bovine serum albumin, bovine serum, culture media components, vector packaging cell or plasmid components, bacteria (e.g., *Alcaligenes faecalis, Escherichia coli, Haemophilus influenzae, Neisseria meningitidis, Pseudomonas aeruginosa, Staphylococcus aureus, Streptococcus pneumoniae*, and *Streptococcus pyogenes* group A), and fungus (*Candida albicans*). The invention is not limited to any particular contaminant. Rather, the invention includes methods of analyses for any contaminant that affects the safety or efficacy of the transduced T cell.

The present invention relates generally to the use of vectors to genetically modify T cells to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8α hinge domain.

With respect to the cytoplasmic domain, the CAR of the invention can be designed to comprise the CD28 and/or 4-1BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof. Accordingly, the invention provides CAR T cells and methods of their use for adoptive therapy.

The invention included methods of producing a vector comprising nucleic acids encoding an anti-CD19 CAR including both CD3-zeta and the 4-1BB costimulatory domain. In one embodiment, the vector comprises a desired CAR, for example a CAR comprising anti-CD19, CD8α hinge and transmembrane domain, and human 4-1BB and CD3zeta signaling domains. The invention is not limited to CARs comprising anti-CD19, but also includes any antigen binding moiety fused with one or more intracellular domains selected from the group of a CD137 (4-1BB) signaling domain, a CD28 signaling domain, a CD3zeta signal domain, and any combination thereof. In preferred embodiments, the vector is a lentiviral vector.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body.

Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal," as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver a nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides methods of analyzing vector supernatants useful for transducing T cells destined for administration to a human subject. The present invention also provides methods of analyzing transduced T cells, and their supernatants, destined for administration to a human subject. In various embodiments, the methods of analysis of the invention include methods of analyzing T cell viability, T cell character (e.g., CD3, CD4, CD8, CD25, CD27, CD45RA, CD57, CD62L, CD95, CD127, CD134, CD244, CCR7, CD40L, CTLA4, PD-1, HLA-DR, TIM3, Ki-67, perforin, and/or granzyme expression), transduction efficiency, the presence and quantity of endotoxin, the presence and quantity of mycoplasma, the presence and quantity of replication competent lentivirus (RCL), the presence and quantity of p24, the presence and quantity of nucleic acid and/or protein derived from each of the plasmids used to package the lentivirus plasmid, the presence and quantity of VSV-G nucleic acid and/or protein, HIVgag, residual anti-CD3/anti-CD28 coated beads, mouse antibodies, pooled human serum, bovine serum albumin, bovine serum, culture media components, vector packaging cell or plasmid components, the presence and quantity of bacteria (e.g., *Alcaligenes faecalis, Escherichia coli, Haemophilus influenzae, Neisseria meningitidis, Pseudomonas aeruginosa, Staphylococcus aureus, Streptococcus pneumoniae*, and *Streptococcus pyogenes* group A), or bacterial products which activate and/or modulate immune system (e.g., LPS, nucleic acid, RNA, etc.), and the presence and quantity of fungus (*Candida albicans*).

In some embodiments, the human subject may have cancer. In various embodiments, the cancer may be a hematological malignancy, a solid tumor, a primary or a metastasizing tumor. Preferably, the cancer is a hematological malignancy, and more preferably, the cancer is Chronic Lymphocytic Leukemia (CLL). Other diseases treatable using the compositions and methods of the invention include viral, bacterial and parasitic infections as well as autoimmune diseases.

In one embodiment, the vector comprises nucleic acid sequences encoding a CAR, wherein when the CAR is expressed by a T cell, the CAR T cell exhibits an antitumor property. The CAR can be engineered to comprise an extracellular domain having an antigen binding domain fused to an intracellular signaling domain of the T cell antigen receptor complex zeta chain (e.g., CD3 zeta). The CAR, when expressed in a T cell is able to redirect antigen recognition based on the antigen binding specificity. An exemplary antigen is CD19 because this antigen is expressed on malignant B cells. However, the invention is not limited to a CAR that recognizes CD19. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is preferably fused with an intracellular domain from one or more of a costimulatory molecule and a zeta chain. Preferably, the antigen binding moiety is fused with one or more intracellular domains selected from the group of a CD137 (4-1BB) signaling domain, a CD28 signaling domain, a CD3zeta signal domain, and any combination thereof.

In one embodiment, the vector of the invention comprises a nucleic acid sequence encoding a CD137 (4-1BB) signaling domain. This is because the CAR-mediated T-cell responses can be further enhanced with the addition of costimulatory domains. For example, inclusion of the CD137 (4-1BB) signaling domain significantly increases anti-tumor activity and in vivo persistence of CAR T cells compared to an otherwise identical CAR T cell not engineered to express CD137 (4-1BB). Methods of genetically modifying T cells with CARs are described in PCT/US11/64191, incorporated herein by reference in its entirety.

Composition

The present invention provides a vector comprising nucleic acids encoding a CAR, wherein the CAR comprises an extracellular and intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the vector of the invention comprises a nucleic acid encoding a CAR, wherein the CAR comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the vector of the invention comprises a nucleic acid encoding a CAR, wherein the CAR is engineered to target a tumor antigen of interest by way of engineering a desired antigen binding moiety that specifically binds to an antigen on a tumor cell. In the context of the present invention, "tumor antigen" or "hyperporoliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding moiety portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention.

In one embodiment, the vector of the invention comprises nucleic acid encoding a CAR, wherein the antigen binding moiety portion of the CAR of the invention targets CD19.

Transmembrane Domain

The transmembrane domain of the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the vector of the invention is the CD8 transmembrane domain. In some instances, the transmembrane domain of the CAR of the invention comprises the CD8α hinge domain.

Cytoplasmic Domain

The cytoplasmic domain or otherwise the intracellular signaling domain of the CAR of the vector of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the vector of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention is exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta.

Vectors

The present invention encompasses methods of producing a vector comprising sequences of a CAR, wherein the sequence comprises the nucleic acid sequence of an antigen binding moiety operably linked to the nucleic acid sequence of an intracellular domain. An exemplary intracellular domain that can be used in the CAR of the vector of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the vector of the invention comprises anti-CD19 scFv, human CD8 hinge and transmembrane domain, and human 4-1BB and CD3zeta signaling domains.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as FICOLL™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a standard centrifuge, a semi-automated "flow-through" centrifuge (for example, the Cobe 2991 cell processor, the Baxter CytoMate, or the Haemonetics CELL SAVER® 5) according to the manufacturer's instructions. After washing, the cells may be resuspended in a variety of biocompatible buffers, such as, for example, $Ca^{2+}$-free, $Mg^{2+}$-free PBS, PlasmaLyte A, 5% Dextrose in 0.45% Sodium Chloride, or other saline solution with or without any combination of buffers. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation or a Miltenyi CliniMACS, or magnetic beads, or magnetic beads coupled to antibodies. A specific subpopulation of T cells, such as $CD3^+$, $CD28^+$, $CD4^+$, $CD8^+$, $CD45RA^+$, $CD45RO^+$, $CD62L^+$, $CD127^+$ T cells, can be further isolated or depleted by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In one embodiment, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-37° C.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan or pentastarch, and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest.

Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) transduced with a vector (e.g., lentiviral vector (LV)). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the CART19 cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, a CART19 cells elicits an immune response specific against cells expressing CD19.

While the data disclosed herein specifically disclose lentiviral vector comprising anti-CD19 scFv derived from FMC63 murine monoclonal antibody, human CD8$\alpha$ hinge and transmembrane domain, and human 4-1BB and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like.

In one embodiment, the CAR can be designed to target CD33/IL3Ra to treat acute myelogenous leukemia and the like.

In one embodiment, the CAR can be designed to target c-Met to treat triple negative breast cancer, non-small cell lung cancer, and the like.

In one embodiment, the CAR can be designed to target PSMA to treat prostate cancer and the like.

In one embodiment, the CAR can be designed to target Glycolipid F77 to treat prostate cancer and the like.

In one embodiment, the CAR can be designed to target EGFRvIII to treat gliobastoma and the like.

In one embodiment, the CAR can be designed to target GD-2 to treat neuroblastoma, melanoma, and the like.

In one embodiment, the CAR can be designed to target NY-ESO-1 TCR to treat myeloma, sarcoma, melanoma, and the like.

In one embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CLL. In certain embodiments, the cells of the invention are used in the treatment of patients at risk for developing CLL. Thus, the present invention provides methods for the treatment or prevention of CLL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v., or i.p., injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Analysis for Contaminants

Lymphocytes transduced to express chimeric antigen receptors (CARs) destined for administration into a human subject are analyzed to detect and quantify possible contaminants introduced during the process of transduction.

General Laboratory Statement

Research sample processing, freezing, and laboratory analyses were performed under principles of Good Manufacturing Practices or Good Laboratory Practices with established SOP and/or protocols for sample receipt, processing, freezing, and analysis.

Vector Production

The CD19-BB-z transgene (GeMCRIS 0607-793) was designed and constructed as described (Milone et al., 2009, Mol Ther. 17:1453-1464). Lentiviral vector was produced according to current good manufacturing practices using a three-plasmid production approach at Lentigen Corporation as described (Zufferey et al., 1997, Nature Biotechnol 15:871-875). A self-inactivating lentiviral vector (GeMCRIS 0607-793) was designed, which was subjected to preclinical safety testing, as reported previously (Milone et al., 2009, Mol Ther, 17: 1453-64). Methods of T-cell preparation have also been described previously (Porter et al, 2006, Blood, 107:1325-31).

Preparation of CART-19 T Cells

Autologous T cells are engineered to express an extracellular single chain antibody (scFv) with specificity for CD19. The extracellular scFv can redirect specificity of the transduced T cells for cells that express CD19, a molecule that is restricted in expression on the surface of the malignant cells and on normal B cells. In addition to CD19 scFv, the cells are transduced to express an intracellular signaling molecule comprised of either the TCR chain or a tandem signaling domain comprised of 4-1BB and TCR signaling modules. The scFv is derived from a mouse monoclonal antibody, and thus contains mouse sequences, and the signaling domains are entirely of the native human sequences. CART-19 T cells are manufactured by isolating the T cells by apheresis, and using lentiviral vector technology (Dropulic et al., 2006, Human Gene Therapy, 17: 577-88; Naldini et al., 1996, Science, 272: 263-7; Dull et al., 1998, J Virol, 72: 8463-71) to introduce the scFv:TCRζ:4-1BB into CD4 and CD8 T cells. In some patients, a control scFv:TCRζ: is introduced into a portion of the cells for a competitive repopulation experiment. These receptors are "universal" in that they bind antigen in an MHC-independent fashion, thus, one receptor construct can be used to treat a population of patients with CD19 antigen-positive tumors.

Figure 2:
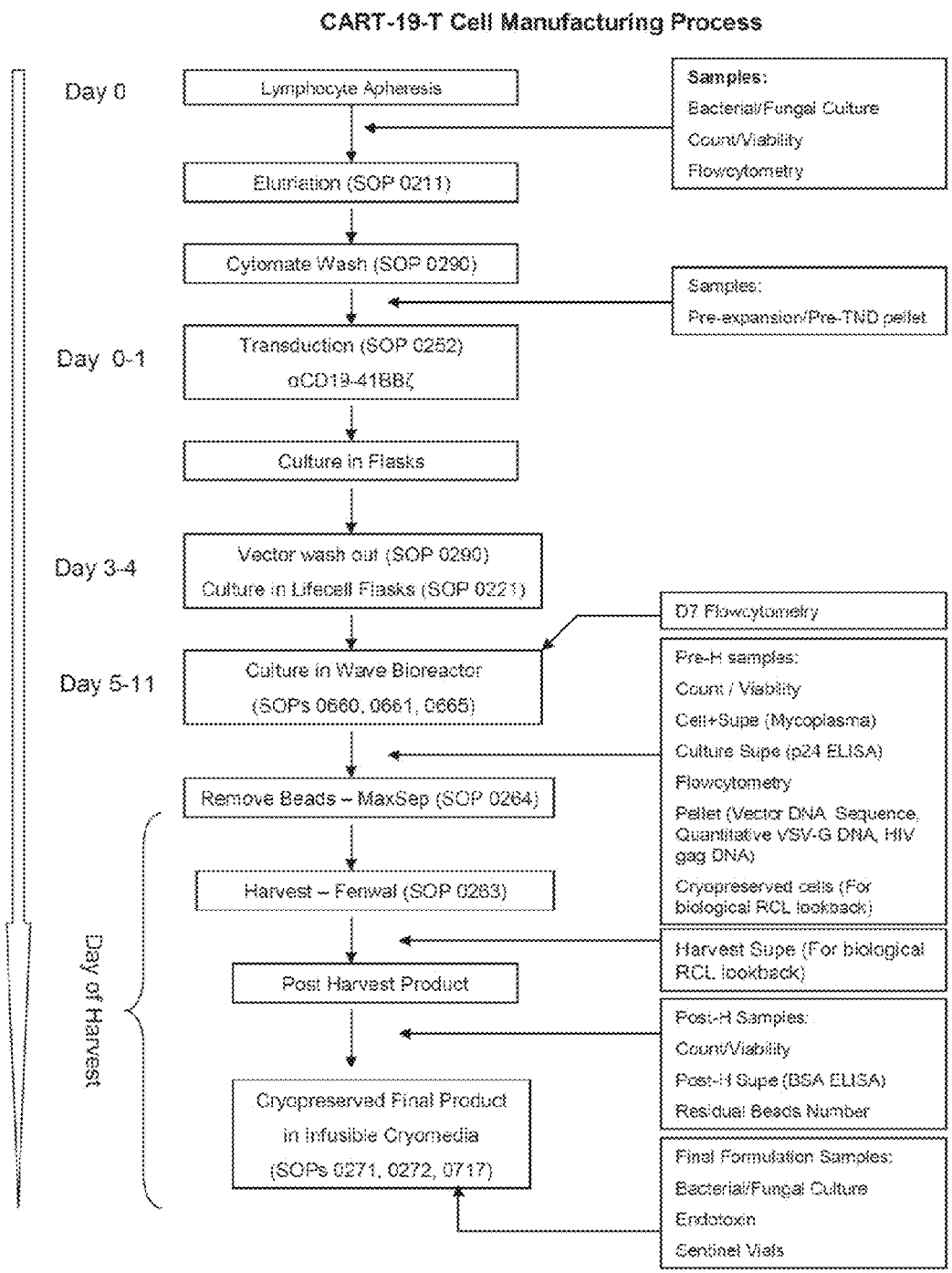
FIG. 2 depicts the manufacturing process of CART-19 cells.
Figure 4:
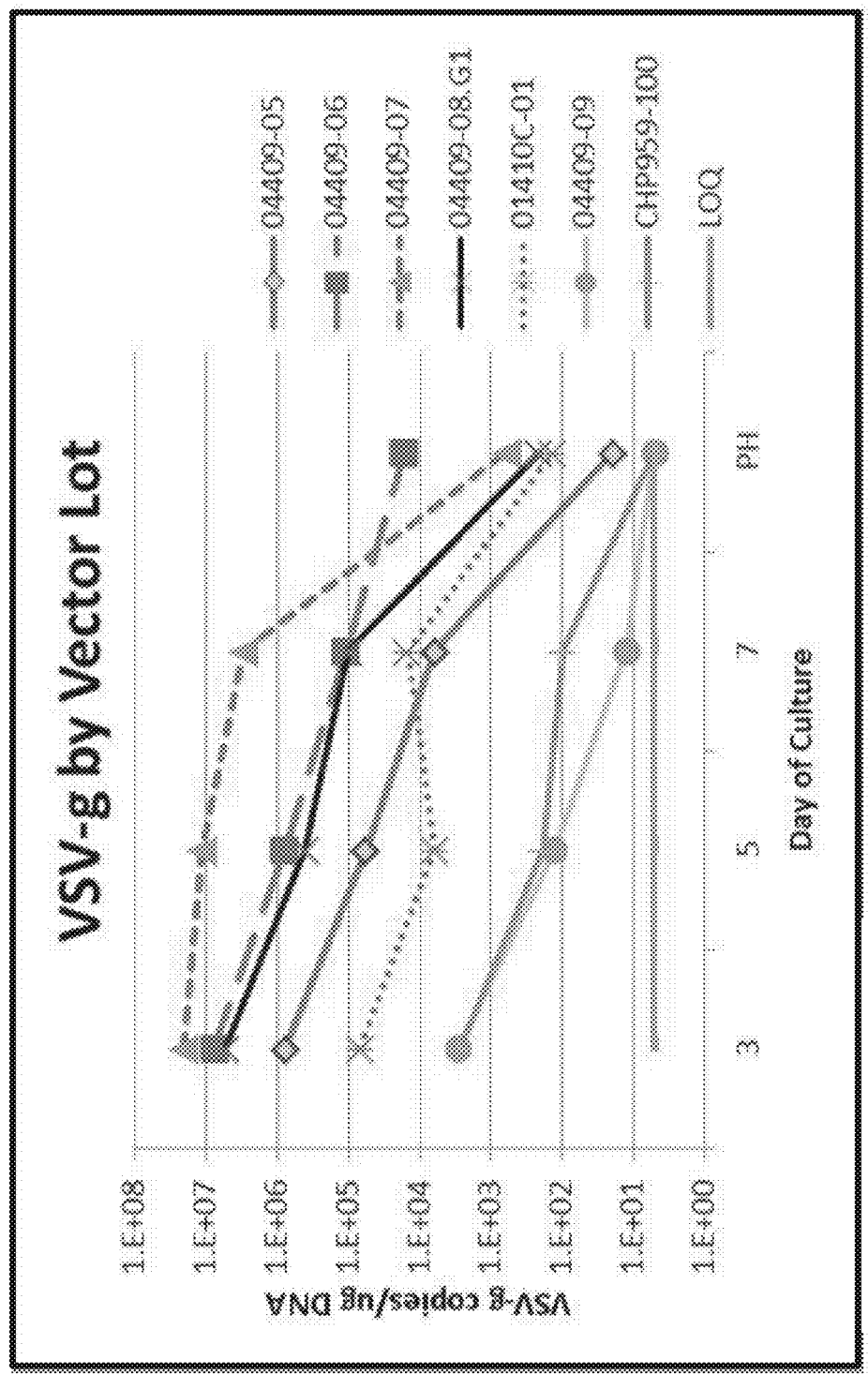
FIG. 4 depicts the results of analyses quantifying VSV-G nucleic acid during the ex vivo culture period.
Figure 5:
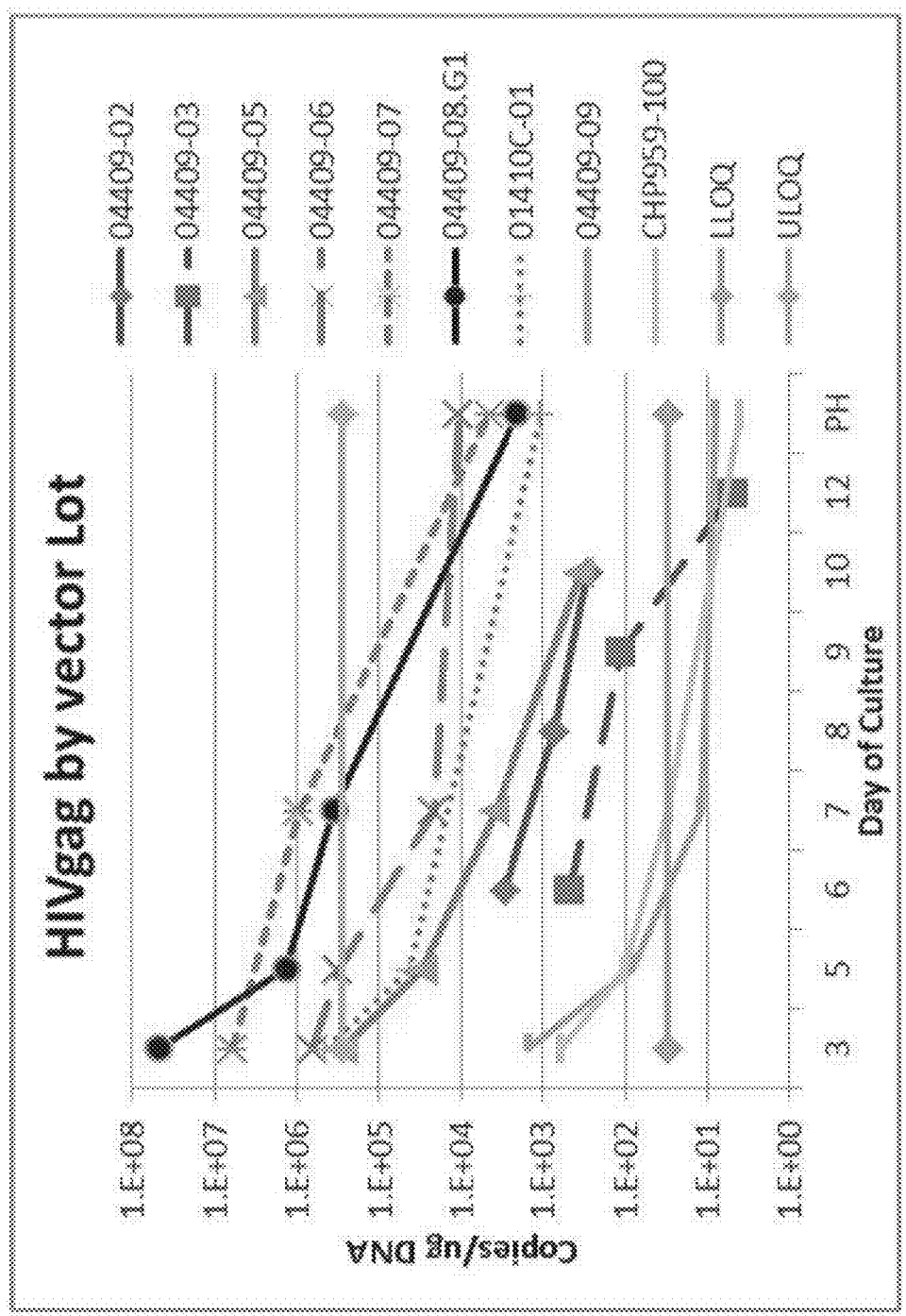
FIG. 5 depicts the results of analyses quantifying HIVgag nucleic acid during the ex vivo culture period.

The CAR constructs were developed at the University of Pennsylvania, and the clinical grade vector was manufactured at Lentigen Corporation. The CART-19 cells are manufactured in the Clinical Cell and Vaccine Production Facility at the University of Pennsylvania according to the process shown in FIG. 2. At the end of cell cultures, the cells are cryopreserved in infusible cryomedia.

T Cell Viability

T cell viability following transduction was determined using a Trypan blue exclusion assay (using 0.4% Trypan Blue Stain (Gibco BRL Cat. No. 15250-061 plus media or diluent and Bright-Line Hemacytometer (Hausser Scientific Company)) or 7-AAD to determine the percentage of living cells (using BD ViaProbe (Cat. No. 555815, BD Biosciences Pharmingen) and flow cytometer.

T Cell Character

The percentage of transduced cells expressing or not expressing particular T cell markers described elsewhere herein was determined using cell staining and flow cytometry.

Transduction Efficiency

The transduction efficiency of T cells was determined using flow cytometry, quantitative PCR or both flow cytometry and quantitative PCR.

Presence and Quantity of Endotoxin

The presence of endotoxin in transduced T cell cultures was assessed using a gel clot assay.

3.1.1 Endosafe PTS-Kinetic reader

Charles River Laboratories, 3.1.2 PTS Logger software 3.1.3 Disposable Inhibition/Enhancement Cartridge Charles River/Cat# PTS220

3.1.4 Disposable LAL cartridge Test Cartridges (0.01-1.0/mL) & C of A for each lot Charles River/Cat# PTS2001F 3.1.5 Disposable LAL cartridge Test Cartridges (0.005-0.5 EU/mL) & C of A for each lot Charles River/Cat# PTS20005F Chromogenic Endpoint assay-read on spectrophotometer 3.1.6 Stop Reagent: 20% w/v Acetic Acid, Glacial Cat # BP2401-212, Fisher Scientific, Pittsburgh, Pa.

Tel: 1-800-766-7000

3.1.7 Limulus Amebocyte Lysate Test Kit

Cat.#50-648U (300 test) or 50-647U (120 test), Cambrex 8830 Biggs Ford Road, Walkersville, Md. 21793

Tel: 800-654-4452, ext. 7822, Fax: 301-845-2924

3.1.7.1 *E. coli* Endotoxin 3.1.7.2 Chromogenic Substrate 3.1.7.3 Chromogenic Limulus Amebocyte Lysate (LAL)

3.1.7.4 LAL Reagent Water (120 test kit only)

3.1.8 LAL Reagent Water

Cat # W50-640, Cambrex, 8830 Biggs Ford Road, Walkersville, Md. 21793

Tel: 800-654-4452, Fax: 301-845-2924

Chromogenic Kinetic assay-read on spectrophotometer 3.1.9 Stop Reagent: 20% w/v Acetic Acid, Glacial Cat # BP2401-212, Fisher Scientific 3.1.10 Limulus Amebocyte Lysate (LAL) Kinetic-QCL Endotoxin Assay Kit Cat.#50-650U (192 tests), Lonza/Cambrex 3.1.10.1 *E. coli* Endotoxin 3.1.10.2 Kinetic-QCL Reagent (a mixture of LAL/Chromogenic Substrate)

LAL Reagent Water

Gel Clot assay 4.1.1 Multi-test Limulus Amebocyte Lysate, PYROGENT® Plus 200 Tests 0.125 EU/mL Sensitivity Cat # N294-125, Lonza 4.1.1.1 Limulus Amebocyte Lysate (LAL) of 0.125 EU/mL sensitivity 4.1.1.1.1 4×50 test vials (5.2 mL/vial)

4.1.1.2 *E. coli* Endotoxin 055:B5, 10 ng/vial, Lyophilized, Control Standard Endotoxin (CSE)

4.1.1.2.1 NOTE: CSE potency in EU/mL is specified on the Certificate of Analysis. The COA is no longer provided with the kit.

4.1.1.2.2 To access a Certificate of Analysis, go to http://www.lonzabio.com/2506.html, enter the Catalog Number and Lot Number located on the product label on the front of the kit box.

4.1.2 LAL Reagent, Lysate sensitivity 0.125 EU/mL (Charles River Laboratories, cat # R11012)

4.1.2.1 Pack of 12

4.1.3 Control Standard Endotoxin 10 ng/vial (Charles River Laboratories, cat # E120_

4.1.3.1 Pack of 6

4.1.4 LAL Reagent Water (LRW), 30 mL/vial

Cat # W130, Charles River Laboratories

Presence and Quantity of Mycoplasma

The presence of mycoplasma in transduced T cell cultures was assessed using a mycoalert assay.

3.1.11 MycoAlert Mycoplasma Detection kit (Lonza, Catalog # LT07-318)-100 tests 3.1.12 MycoAlert Assay Control Set (Lonza Catalog # LT07-518)

3.1.13 96 well, opaque, white bottom micro-plates (Corning Incorporated catalog #3912)

Corning Incorporated Life Sciences 45 Nagog Park, Acton Mass. 01720

Tel: 1-978-635-2200, Fax: 1-978-635-2476

Read on luminometer.

MycoProbe Mycoplasma ELISA.

Presence and Quantity of Replication Competent Lentivirus (RCL)

The presence of RCL in transduced T cell cultures was assessed using a PCR assay assessing for VSV-G and HIVgag, and ELISA for p24.

Presence and Quantity of p24

The presence of p24 in transduced T cell cultures was assessed using an ELISA assay.

5.1.1 PerkinElmer HIV-1 p24 ELISA Kit

Cat. No. NEK050 (1×96-well plate),

NEK050A (2×96-well plates)

NEK050B (5×96-well plate)

PerkinElmer, Inc, 940 Winter Street, Waltham, Mass. 02451,

Tel: 800-762-4000

Presence and Quantity of VSV-G Nucleic Acid

The presence of VSV-G nucleic acid in transduced T cell cultures was assessed using a quantitative PCR assay using a primer/probe combination that specifically amplifies and detects VSV-G sequences under standard ABI amplification conditions. A qualified QPCR assay to quantify VSV-G DNA using the above primers has been established. The qualified assay utilizes a standard curve generated from genomic DNA isolated from PBMC spiked with the plasmid pC1-VSV-G which contains the VSV-G gene sequence; the standard curve ranges from 1×106-10 copies VSV-G/100 ng PBMC. For each final product the presence of residual VSV-G DNA is evaluated in triplicate reactions using approximately 200 ng genomic DNA isolated from the product. The amount of residual VSV-G plasmid is determined from the standard curves and reported as copies VSV-G plasmid/microgram genomic DNA after correcting and normalizing for amount of input DNA. The presence of contaminating plasmid nucleic acid for each of the additional packaging plasmids (LIST) can be determined in this manner using primer/probe combinations specific for each plasmid used in the packaging step (VSVG, Gag pol, P24, pRSV.rev).

Presence and Quantify of Bacteria

The presence of bacteria in transduced T cell cultures was assessed by attempting to culture bacteria using material from the transduced T cell cultures. The BACTEC assay is used to test for bacterial contamination. BACTEC culture vials support the growth of common aerobic microorganisms, and they are inoculated by sterile syringe containing 1-3 ml of culture medium. Detection of growth is performed using the BACTEC 9050 instrument, which measures increases in $CO_2$ concentration over time. This assay is performed at the CVPF in accordance with SOP 0361, which is provided elsewhere herein. The sensitivity of this test in the CVPF laboratory has not been confirmed, but published studies indicate that the BACTEC is more sensitive, faster in time to detection, less prone to false-positive results than the CFR method (Khuu et al, 2004 and 2006).

Presence and Quantity of Fungus

The presence of fungus in transduced T cell cultures was assessed by attempting to culture bacteria using material from the transduced T cell cultures. Testing for fungal contamination is performed at the HUP Clinical Microbiology laboratories using Sabouraud Brain Heart Infusion Agar based on the formulation of Gorman, 1967. The media is optimized to improved fungal recovery, and also contains various antimicrobial agents to impede the outgrowth of bacteria that might compete with fungal growth. Culture medium is inoculated by streaking. Cultures are followed for 14 days to be determined negative. The sensitivity of this assay has not been determined by the Clinical Microbiology Laboratory. Positive controls for this assay include three fungi, *Blastomyces dermatitidis, Candida albicans*, and *Trichophyton mentagrophytes*, which should grow to indicate viable media. To monitor for the potency of the antimicrobial agents, control plates are inoculated with *Escherichia coli* and partial to complete inhibition should be observed.

Storage

Bags (10 to 100 ml capacity) containing CART-19-transduced T cells are stored in blood bank conditions in a monitored −135° C. freezer. Infusion bags are stored in the freezer until needed.

Cell Thawing

After logging the cells in the investigational pharmacy, frozen cells are transported in dry ice to the subject's bedside. The cells are thawed at the bedside one bag at a time using a water bath maintained at 36° C. to 38° C. The bag is gently massaged until the cells have just thawed. There should be no frozen clumps left in the container.

Administration/Infusion

Infusions begin 1 to 2 days after completion of chemotherapy. The day of the first infusions, patients have a CBC with differential, and assessment of CD3, CD4 and CD8 counts since chemotherapy is given in part to induce lymphopenia. Without wishing to be bound by any particular theory, it is believed that an initial i.v. dose of $2.5-5 \times 10^9$ CART-19 cells is optimal for this protocol. Because there are about $1 \times 10^{12}$ T cells in a healthy adult, the proposed total dose is equivalent to about 0.5% of the total body mass of T cells (Roederer, 1995, Nat Med, 1: 621-7; Macallan et al., 2003, Eur J Immunol, 33: 2316-26). The first dose is administered using a split dose on days 0 (10%), 1 (30%) and 2 (60%). Subjects receive infusion in an isolated room.

The cells are thawed at the patient's bedside as described elsewhere herein. The thawed cells are given at an infusion rate as quickly as tolerated so that the duration of the infusion is approximately 10-15 minutes. The transduced T cells are administered by rapid intravenous infusion at a flow rate of approximately 10 mL to 20 mL per minute through an 18-gauge latex free Y-type blood set with a 3-way stopcock. The duration of the infusion is approximately 15 minutes. One or two bags of CART-19 modified cells are delivered on ice, and the cells are administered to the subject while cold. In subjects receiving mixtures of CART-19 cells, in order to facilitate mixing, the cells are administered simultaneously using a Y-adapter. Subjects are infused and premedicated as described elsewhere herein. Subjects' vital signs are assessed and pulse oximetry is done prior to dosing, at the end of the infusion and every 15 minutes thereafter for 1 hour and until these are stable and satisfactory. A blood sample for determination of baseline CART-19 level is obtained before infusion and 20 minutes post infusion. Patients experiencing toxicities from their preceding cytoreductive chemotherapy have their infusion schedule delayed until these toxicities have resolved. The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management. 3) Hypotension requiring pressor support. 4) Active Infection: Positive blood cultures for bacteria, fungus, or virus within 48-hours of T cell infusion. A serum sample for potassium and uric acid is collected before the first infusion as well as two hours after each subsequent infusion.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of analyzing a composition comprising a genetically modified T cell to detect a contaminant, the method comprises:
preparing the composition comprising the genetically modified T cell, wherein the genetically modified T cell comprises a nucleic acid encoding a chimeric antigen receptor (CAR) comprising an antigen binding domain, a transmembrane domain, a costimulatory signaling region, and a signaling domain; and
analyzing the composition for at least one contaminant selected from the group consisting of a replication competent lentivirus (RCL), p24, a nucleic acid and/or protein derived from a plasmid used to package a lentivirus plasmid, vesicular stomatitis virus G-protein (VSV-G) nucleic acid and/or protein, and human immunodeficiency virus (HIV) gag.

2. The method of claim 1, wherein preparing the composition further comprises genetically modifying the T cell by transduction with a lentiviral vector.

3. The method of claim 1, wherein the contaminant further comprises at least one selected from the group consisting of endotoxin, mycoplasma, residual anti-CD3/anti-CD28 coated beads, mouse antibodies, pooled human serum, bovine serum albumin, bovine serum, culture media components, vector packaging cell or plasmid components, a bacterium and a fungus.

4. The method of claim 3, wherein the bacterium is at least one selected from the group consisting of *Alcaligenes faecalis, Escherichia coli, Haemophilus influenzae, Neisseria meningitidis, Pseudomonas aeruginosa, Staphylococcus aureus, Streptococcus pneumoniae*, and *Streptococcus pyogenes* group A.

5. The method of claim 1, wherein the signaling domain is a cluster of differentiation 3 (CD3) zeta signaling domain.

6. The method of claim 1, wherein the antigen binding domain is an antibody or an antigen-binding fragment thereof.

7. The method of claim 6, wherein the antigen-binding fragment is a fragment antigen binding (Fab) or a single chain variable fragment (scFv).

8. The method of claim 1, wherein the antigen binding domain binds to a tumor antigen.

9. The method of claim 8, wherein the tumor antigen is associated with a hematologic malignancy.

10. The method of claim 8, wherein the tumor antigen is associated with a solid tumor.

11. The method of claim 8, wherein the tumor antigen is selected from the group consisting of CD19, CD20, CD22, receptor tyrosine kinase-like orphan receptor 1 (ROR1), mesothelin, CD33/interleukin 3 receptor alpha (IL3Ra), c-Met, prostate-specific membrane antigen (PSMA), Glycolipid F77, epidermal growth factor receptor variant III (EGFRvIII), GD-2, NY-ESO-1 T cell receptor (TCR), melanoma antigen 3 (MAGE A3) TCR, and any combination thereof.

12. The method of claim 1, wherein the costimulatory signaling region comprises the intracellular domain of a costimulatory molecule selected from the group consisting of CD27, CD28, 4-1BB, OX40, CD30, CD40, programmed cell death protein 1 (PD-1), inducible T cell co-stimulator (ICOS), lymphocyte function-associated antigen-1 (LFA-1), CD2, CD7, homologous to lymphotoxin, exhibits inducible expression and competes with HSV glycoprotein D for binding to herpesvirus entry mediator, a receptor expressed on T lymphocytes (LIGHT), NKG2C, B7-H3, a ligand that specifically binds with CD83, and any combination thereof.

13. The method of claim 1, wherein the contaminant is quantified to determine an effect on safety or efficacy of the composition comprising the genetically modified T cell.

14. The method of claim 1, wherein the contaminant is compared with a corresponding control level to determine an effect on safety or efficacy of the composition comprising the genetically modified T cell.

* * * * *

UNITED STATES PATENT AND TRADEMARK OFFICE
CERTIFICATE OF CORRECTION

PATENT NO. : 9,572,836 B2
APPLICATION NO. : 14/412844
DATED : February 21, 2017
INVENTOR(S) : Carl H. June, Bruce L. Levine and Michael D. Kalos It is certified that error appears in the above-identified patent and that said Letters Patent is hereby corrected as shown below:

In the Specification

On Column 1, Line 20, replace the paragraph after "STATEMENT REGARDING FEDERALLY SPONSORED RESEARCH OR DEVELOPMENT" with the following paragraph:
-- This invention was made with government support under grant number CA117879, EY016586, CA105216, CA120409 and AI057838 awarded by the National Institutes of Health. The government has certain rights in the invention. --

Signed and Sealed this
Fourth Day of September, 2018

Andrei Iancu
*Director of the United States Patent and Trademark Office*